United States Patent [19]

Suzuki et al.

[11] Patent Number: 5,026,833

[45] Date of Patent: Jun. 25, 1991

[54] 4$^G$-ALPHA-D-GLUCOPYRANOSYL RUTIN, AND ITS PREPARATION AND USES

[75] Inventors: Yukio Suzuki; Kei Suzuki; Masaru Yoneyama; Toshio Miyake, all of Okayama, Japan

[73] Assignee: Kabushiki Kaisha Hayashibara Seibutsu Kagaku Kenkyuju, Okayama, Japan

[21] Appl. No.: 489,568

[22] Filed: Mar. 7, 1990

[30] Foreign Application Priority Data

Sep. 28, 1989 [JP] Japan .................................. 1-253269

[51] Int. Cl.$^5$ ...................... C07H 15/24; C07H 15/00
[52] U.S. Cl. ......................................... 536/18.1; 536/8
[58] Field of Search .................................. 536/8, 18.1

[56] References Cited

FOREIGN PATENT DOCUMENTS 54-32073 10/1979 Japan .

Primary Examiner—Thurman Page
Assistant Examiner—G. S. Kishore
Attorney, Agent, or Firm—Browdy and Neimark

[57] ABSTRACT

A novel glycoside, 4$^G$-alpha-D-glucopyranosyl rutin, is formed by a saccharide-transferring enzyme and glucoamylase in a solution which contains rutin together with glucoamylase. The 4$^G$-alpha-D-glucopyranosyl rutin formed in such a solution is purified with a synthetic macroreticular resin, and crystallization in an organic solvent yields a complex crystal with the organic solvent. 4$^G$-Alpha-D-glucopyranosyl rutin exhibits the same molecular absorption coefficient as intact rutin, and is readily water-soluble, substantially tasteless and odorless, and readily hydrolyzable in vivo to exhibit physiological activities inherent to rutin. These render 4$^G$-alpha-D-glucopyranosyl rutin very useful as a highly-safe, natural yellow coloring agent, antioxidant, stabilizer, quality-improving agent, preventive, remedy, uv-absorbent and deterioration-preventing agent in foods, beverages, tobaccos, cigarets, feeds, pet foods, pharmaceuticals, cosmetics and plastics.

1 Claim, 3 Drawing Sheets

4$^G$-ALPHA-D-GLUCOPYRANOSYL RUTIN, AND ITS PREPARATION AND USES

BACKGROUND OF THE INVENTION

1. Field of the Invention

The present invention relates to 4$^G$-alpha-D-glucopyranosyl rutin shown by the formula [I]:

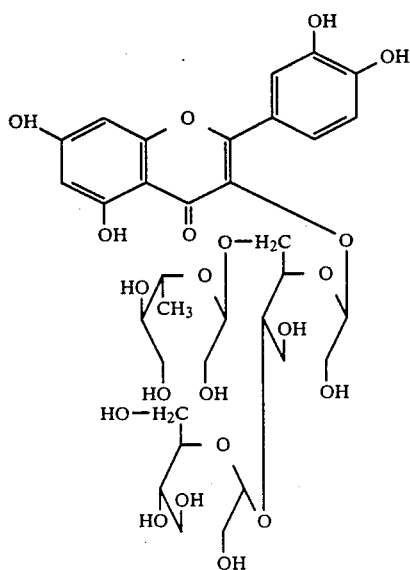

and its preparation and uses.

2. Description of the Prior Art

Rutin, which has a chemical structure shown with the formula [II]:

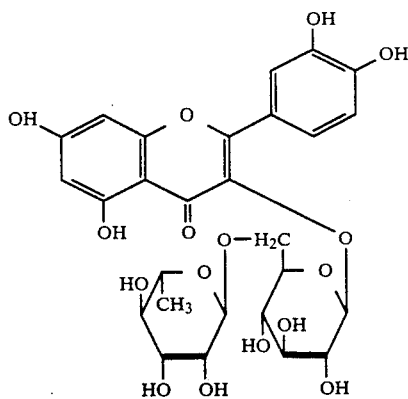

has been known as a yellow pigment and vitamin P with physiological activities such as stabilization of blood vessel, prevention of hemorrhage and regulation of blood pressure, and has been used from ancient times in foodstuffs, pharmaceuticals and cosmetics.

It is known that vitamin P takes part in some physiological activities of vitamin C in vivo; for example, in the hydroxylation of proline and lysine which are necessary to synthesize collagen as the main element of living connective tissues; the oxidation-reduction reaction of cytochrome C wherein $Fe^{+++}$ is reduced to $Fe^{++}$; and in the immunopotentiation via the increase of leukocyte. These are because vitamin P plays a significant role in the maintenance and promotion of health in living bodies.

Nowadays the use of rutin is not limited to agents which enrich vitamin P as a nutritive element, but is extending in various applications. More particularly, because of the chemical structure and physiological activities, rutin is useful as a yellow coloring agent and antioxidant alone or in combination with one or more vitamins, for example, in foods, beverages and pharmaceuticals for susceptive diseases such as a preventive and remedy for circulatory diseases, as well as a yellow coloring agent and uv-absorbent in cosmetics such as skin-refining and skin-whitening agents.

Rutin is, however, hardly soluble in water (only about 1 g in 8 liters of water or about 0.01 w/v % at ambient temperature). This renders its practical use very difficult.

To improve this low water-solubility, some methods have been attempted. For example, Japanese Patent Publication No. 1,677/50 disclose a method wherein aliphatic compounds with amino groups are added to rutin for its increased water-solubility; Japanese Patent Publication No. 2,724/51, another method wherein monohalogeno acetic acids are allowed to act on rutin to convert it into sodium monohalogeno acetates having an increased water-solubility; and Japanese Patent Publication No. 1,285/54, one another method wherein "Rongalit", a commercialized sodium hydroxymethane, is allowed to act on rutin to convert it into sulfite compounds having an increased water-solubility.

These methods have, however, the drawback that the use of amino compounds, monohalogeno acetic acids and sulfite compounds may result in an undesirable physiological activity and/or toxicity in final products, as well as rendering their purification very difficult.

We proposed a much safer solubilization method in Japanese Patent Publication No.32,073/79, wherein a bio-synthesis by saccharide-transferring enzyme is utilized to transfer equimolar or more glucose residues from a partial starch hydrolysate to rutin to form alpha-glycosyl rutin having an improved water-solubility.

Japanese Patent Publication No. 32,073/79 describes the conversion of rutin into a mixture of rutin glycosides wherein equimolar or more glucose residues are bound for an improved water-solubility, but does not characterize particular glycosides.

This is obvious from Table in page 3 of the Japanese Patent Publication, which describes that the designation of glycosides is based on the speculation, and the position to which glucose residues are newly transferred has not been clarified.

To extend the application of alpha-glycosyl rutin, characterization of glycosides has been in long expectation. Realization of novel glycosides with a clarified chemical structure has been in strong demand.

SUMMARY OF THE INVENTION

The present invention is to solve the above described object. We studied particularly the physicochemical properties of alpha-glucosyl rutin having the lowest molecular weight among those which are formed by a saccharide-transferring enzyme, as well as studying its preparation and uses.

As the result, we characterized 4$^G$-alpha-D-glucopyranosyl rutin, a novel substance shown the formula [I], and established its preparation and uses.

We found that 4$^G$-alpha-D-glucopyranosyl rutin has a strong antioxidant activity and an extremely high water-solubility which is about thirty thousand-fold or much higher than that of intact rutin, and its molecular absorption coefficient or degree of yellowness is substantially the same as that of rutin, as well as that $4^G$-alpha-D-glucopyranosyl rutin is an ideal substance because it is readily hydrolyzable by the in vivo alpha-glucosidase to exhibit physiological activities inherent to rutin.

Furthermore, we established a process to prepare high-purity $4^G$-alpha-D-glucopyranosyl rutin which comprises crystallizing $4^G$-alpha-D-glucopyranosyl rutin in a super-saturated solution in an organic solvent, and recovering the resultant crystal. This facilitates the preparation and commercialization of a substantially non-hygroscopic high-purity powdery product.

We also found that $4^G$-alpha-D-glucopyranosyl rutin is obtainable by allowing a saccharide-transferring enzyme and glucoamylase to act on a solution containing rutin together with an amylaceous substance to form $4^G$-alpha-D-glucopyranosyl rutin, and recovering the resultant $4^G$-alpha-D-glucopyranosyl rutin.

DETAILED DESCRIPTION OF THE INVENTION

Figure 1:
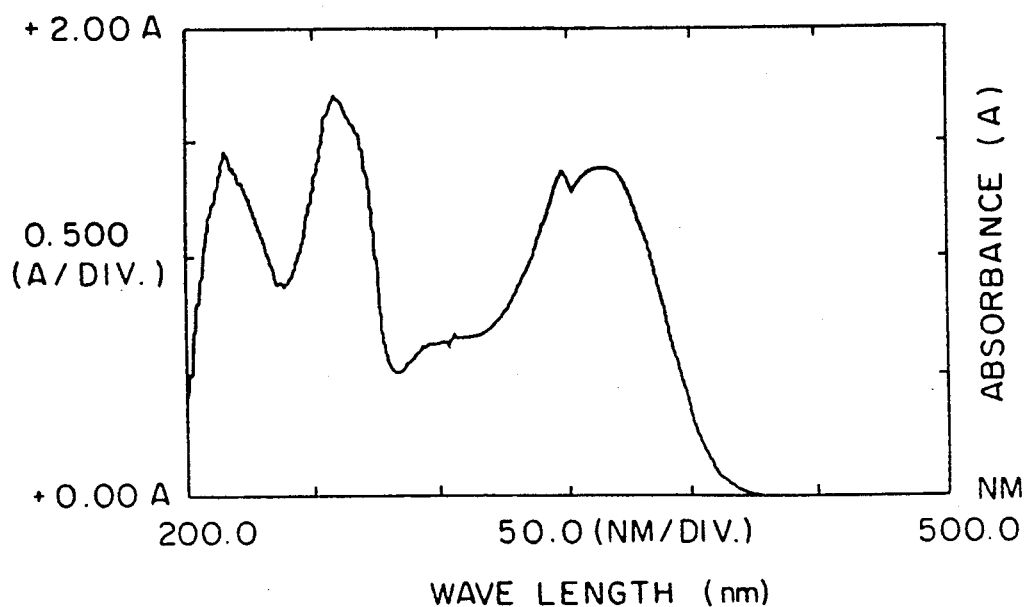
FIG. 1 shows a uv-absorption spectrum of $4^G$-alpha-D-glucopyranosyl rutin.

Generally, a highly-purified rutin is favorably usable in the invention. If necessary, intact and partially-purified extracts from plant tissues are suitable, as long as they contain rutin.

Examples of such plant tissues are leaves and stems of buckwheat plant (*Fagopyrum esculentum*), eucalyptus and ginkgo tree (*Ginkgo biloba*); "kaika" or "kaibei", flower buds of Japanese pagoda tree (*Sophora japonica*); flower buds of common broom (*Cytisus scoparius*); citrus fruits; and their tissue culture.

The amylaceous substances usable in the invention are those which permit a saccharide-transferring enzyme to act on rutin to form alpha-glycosyl rutin wherein equimolar or more glucose residues are bound to rutin. For example, partial starch hydrolysates such as amylose, dextrin, cyclodextrin and maltooligosaccharide, liquefied starch, and gelatinized starch can be suitably chosen.

Consequently to facilitate the formation of alpha-glycosyl rutin, it is recommendable to choose for particular saccharide-transferring enzyme an amylaceous substance having an adequate susceptivity thereto.

For example, in the case of using alpha-glucosidase (EC 3.2.1.20) as the saccharide-transferring enzyme, malto-oligosaccharides such as maltose, maltotriose and maltotetraose are suitable, as well as partial starch hydrolysates having a DE (dextrose equivalent) in the range of about 10–70. When cyclomaltodextrin glucanotransferase (EC 2.4.1.19) is used as the saccharide-transferring enzyme, gelatinized starches having a DE of below 1 and partial starch hydrolysates having a DE up to about 60 are suitable, as well as cyclodextrins. When alpha-amylase (EC 3.2.1.1) is used as the saccharide-transferring enzyme, gelatinized starches having a DE of below 1 and dextrins and partial starch hydrolysates having a DE up to about 30 are suitable.

The concentration of such an amylaceous substance during the reaction is set to a level which is about 0.5–50-fold higher than that of rutin.

The wording "solution containing rutin together with an amylaceous substance" as referred to in the invention means those which contain rutin, desirably, at the possible highest concentration. For example, a solution which contains rutin at a high concentration, and is obtainable by either dissolution at an alkaline pH exceeding 7.0 or dissolution in an aqueous organic solvent is suitable, as well as a suspension which contains rutin at a high concentration. More particularly, the wording means suspension and solution which have a rutin content of about 0.5 w/v % or higher, desirably, about 1.0–20.0 w/v % when calculated as rutin.

The saccharide-transferring enzymes usable in the present invention are those which form alpha-glycosyl rutin without decomposing rutin when allowed to act on a solution which contains rutin together with an amylaceous substance having an adequate susceptivity to the enzyme.

Examples of such a saccharide-transferring enzyme are alpha-glucosidases derived from animal and plant tissues such as pig liver and buckwheat seed, and from a culture obtainable by cultivating in a nutrient culture medium microorganisms including bacteria, molds and yeasts, for example, those of the genera Mucor, Penicillium and Saccharomyces; cyclomaltodextrin glucanotransferases derived from a culture of bacteria such as those of the genera Bacillus and Klebsiella; and alpha-amylases derived from a culture of fungi such as those of the genus Aspergillus.

Such a saccharide-transferring enzyme should not necessarily be purified prior to its use, as long as it fulfills the above requirements. Generally, the present invention is feasible with a crude enzyme.

If necessary, saccharide-transferring enzymes can be purified by conventional method, prior to its use. Of course, commercialized saccharide-transferring enzymes can be used in the invention.

In the course of the reaction, the pH and temperature are set to a level where a saccharide-transferring enzyme forms alpha-glycosyl rutin; usually, at a pH in the range of 3–10 and a temperature in the range of 10–90° C.

The amount of saccharide-transferring enzyme and reaction time are closely dependent each other. With an economical viewpoint, saccharide-transferring enzyme is used in an amount which completes the reaction within about 5–80 hours.

Immobilized saccharide-transferring enzymes can be suitably used batchwise and in continuous manner.

If necessary, alpha-glycosyl rutin can be produced by culturing a microorganism capable of producing a saccharide-transferring enzyme in a nutrient culture medium which contains rutin together with an amylaceous substance, or incubating in such a nutrient culture medium an animal- or plant-tissue which contains a saccharide-transferring enzyme.

The present invention is feasible with any reaction process, as long as it contains the step of allowing a saccharide-transferring enzyme and glucoamylase (EC 3.2.1.3) to act on a solution which contains rutin together with an amylaceous substance.

Any glucoamylase can be used in the invention, regardless of its origin such as microorganism and plant: Usually, commercialized glucoamylases derived from microorganisms such as those of the genera Aspergillus and Rhizopus are favorably usable.

Glucoamylase can be used simultaneously with a saccharide-transferring enzyme in the formation of $4^G$-alpha-D-glucopyranosyl rutin.

Generally, in order to efficiently utilize an amylaceous substance, desirably; a saccharide-transferring enzyme is first allowed to act on the amylaceous substance to form an alpha-glycosyl rutin wherein equimolar or more glucose residues are transferred, then glucoamylase is allowed to act on the alpha-glycosyl rutin to accumulate $4^G$-alpha-D-glucopyranosyl rutin. Beta-amylase (EC 3.2.1.2) can be freely used in combination with glucoamylase.

The reaction process using a saccharide-transferring enzyme will be explained at first.

In the course of the reaction, the concentration of rutin is brought to the possible highest level in view of commercialization.

For example, in case that rutin is allowed to react at a high concentration in suspension, a high-rutin content liquid which contains in suspension about 0.5 w/v % or more, desirably, about 1.0–5.0 w/v % of rutin together with an appropriate amount of an amylaceous substance is subjected to a saccharide-transferring enzyme while keeping the pH to about 4.5–6.5 and the temperature to the possible highest level where the saccharide-transferring enzyme is active, in particular, in the range of about 65–95° C. Thus, as the conversion into alpha-glycosyl rutin proceeds, the rutin in suspension gradually dissolves to promptly and readily form alpha-glycosyl rutin at a high concentration wherein equimolar or more glucose residues are bound to rutin.

For example, in case that rutin is allowed to react in a high-concentration solution obtainable by dissolving rutin at an alkaline pH exceeding 7.0, a high-rutin content liquid which is obtainable by first dissolving about 0.5 w/v % or more, desirably, about 1.0–5.0 w/v % rutin in water at pH 7.5–10 by heating, then dissolving in the resultant solution an appropriate amount of an amylaceous substance is subjected to a saccharide-transferring enzyme while keeping both pH and temperature to the possible highest levels where the saccharide-transferring enzyme is active, in particular, at a pH in the range of about 7.5–10.0 and a temperature in the range of about 50–80° C. Thus, alpha-glycosyl rutin is readily formed at a high concentration.

In this case, since rutin tends to readily decompose in an alkaline solution, desirably, the liquid is kept under light-shielding and an aerobic conditions in order to prevent the decomposition.

For example, in case that rutin is allowed to react in a high-concentration solution in an aqueous organic solvent, a solution which is obtainable by dissolving rutin in an organic solvent by heating is mixed with an amylaceous substance in aqueous solution, and then added with a saccharide-transferring enzyme. Alternatively, rutin and an amylaceous substance are dissolved in an aqueous organic solvent by heating, and the resultant solution is cooled to a prescribed temperature and added with a saccharide-transferring enzyme. Thus, alpha-glycosyl rutin is formed at a high concentration.

Alpha-glycosyl rutin can be formed at a high concentration similarly as above by the combination of two or more procedures; for example, by allowing a saccharide-transferring enzyme to act a high-rutin content liquid which contains in suspension an about 2.0–20.0 w/v % rutin together with an appropriate amount of an amylaceous substance while keeping the liquid at a pH in the range of about 7.5–10.0 and a temperature in the range of 50–80° C.

Also alpha-glycosyl rutin can be readily formed at a high concentration by dissolving rutin in a strongly alkaline aqueous solution, for example, about 0.1–1.0N aqueous solutions of sodium hydroxide, potassium hydroxide, sodium carbonate, calcium hydroxide and ammonia, to give a concentration of about 5.0–20.0 w/v %; adjusting the resultant solution with an aqueous solution of an acid such as hydrochloric acid and sulfuric acid to a pH level where a saccharide-transferring enzyme is active; adding an amylaceous substance to the solution; and promptly subjecting the solution to the enzyme.

To prepare $4^G$-alpha-D-glucopyranosyl rutin from the alpha-glycosyl rutin formed by the saccharide-transfer reaction, a reaction mixture is subjected to glucoamylase intact or after inactivating the saccharide-transferring enzyme by heating. Glucoamylase hydrolyzes higher polymers of alphaglycosyl rutin to accumulate D-glucose and $4^G$-alpha-D-glucopyranosyl rutin.

The obtained reaction mixture, which usually contains $4^G$-alpha-D-glucopyranosyl rutin and a relatively large amount of the remaining rutin, may be prepared into final products without no further special treatment. Usually, the reaction mixture is filtered and concentrated into a syrupy product which is, if necessary, dried and prepared into a powdery product.

The products are favorably usable as a highly-safe, natural yellow coloring agent, antioxidant, stabilizer, quality-improving agent, preventive, remedy and uv-absorbent in foods, beverages, tobaccos, cigarets, feeds, pet foods, pharmaceuticals for susceptive diseases, cosmetics and plastics, in addition to the use in vitamin P-enriching agents. In case that a purified $4^G$-alpha-D-glucopyranosyl rutin product is needed, $4^G$-alpha-D-glucopyranosyl rutin and contaminants including glucose are separated, for example, by utilizing the difference in adsorbability to a synthetic macroreticular resin.

The wording "synthetic macroreticular resin" as referred to in the invention means non-ionic, porous, synthetic resins which provide a large adsorptive area, such as styrenedivinylbenzene copolymer, phenol-formaldehyde resin, acrylic resin and methacrylate resins. Examples such as such a resin are "Amberlite XAD-1", "Amberlite XAD-2", "Amberlite XAD-4", "Amberlite XAD-7", "Amberlite XAD-8", "Amberlite XAD-11" and "Amberlite XAD-12", products of Rohm & Haas Company, Philadelphia, USA; "Diaion HP-10", "Diaion HP-20", "Diaion HP-30", "Diaion HP-40" and "Diaion HP-50", products of Mitsubishi Chemical Industries Ltd., Tokyo, Japan; and "Imac Syn-42", "Imac Syn-44" and "Imac Syn-46", products of Industrie de Maatshappily activate N.V., Amsterdam, Netherlands.

The purification process according to the invention contains the step of applying a reaction mixture containing $4^G$-alpha-D-glucopyranosyl rutin, for example, to a column of a synthetic macroreticular resin so that the column adsorbs the $4^G$-alpha-glucopyranosyl rutin and a relatively small amount of the remaining rutin, while large amounts of water-soluble saccharides including glucose flows out through the column without causing adsorption.

Particularly in case that a reaction mixture contains an organic solvent, $4^G$-alpha-D-glucopyranosyl rutin can be purified similarly as above by first decreasing the concentration of the organic solvent, then allowing the reaction mixture to contact a synthetic macroreticular resin such that it adsorbs the $4^G$-alpha-D-glucopyranosyl rutin.

If necessary, after completion of the saccharidetransfer reaction but before treatment with a synthetic macroreticular resin, the reaction mixture can be treated by one or more methods; for example, a method wherein the reaction mixture is heated and the insolubilized substances are removed by filtration; another method wherein the reaction mixture is treated, for example, with either magnesium alumino silicate hydrate or magnesium aluminate to adsorb the proteinaceous substances for their removal; and another method wherein the reaction mixture is deionized with a strongly-acidic ion exchange (H-form) and/or a neutral or slightly-alkaline ion exchange (OH-form).

A column of a synthetic macroreticular resin on which $4^G$-alpha-D-glucopyranosyl rutin and a relatively small amount of the remaining rutin are specifically adsorbed are washed with a diluted alkali or water, and then applied with a relatively small amount of an organic solvent or mixture with water, for example, aqueous methanol and aqueous ethanol. Thus, the $4^G$-alpha-D-glucopyranosyl rutin first elutes, while the intact rutin can be eluted by continuing the application or increasing the concentration of the organic solvent.

The obtained eluate rich in $4^G$-alpha-D-glucopyranosyl rutin is distilled to remove the organic solvent, and concentrated to an adequate level. Thus, one can obtain a syrupy product mainly composed of $4^G$-alpha-D-glucopyranosyl rutin. Subsequent drying and pulverization of the product yield a powdery product mainly composed of $4^G$-alpha-D-glucopyranosyl rutin.

The elution operation for $4^G$-alpha-D-glucopyranosyl rutin and remaining rutin using organic solvents simultaneously regenerates synthetic macroreticular resins, and this enables its repeated use.

The purification process using synthetic macroreticular resins is characterized in that it can remove, in addition to water-soluble saccharides such as glucose, other concomitants including water-soluble salts.

If necessary, a pure $4^G$-alpha-D-glucopyranosyl rutin can be obtained by using other one or more procedures, for example, separation utilizing the difference in solubility, molecular weight fractionation, membrane separation, high-performance liquid chromatography and column chromatography solely or in combination with the above described procedure using synthetic macroreticular resins.

The following will explain the preparation of a much purer $4^G$-alpha-D-glucopyranosyl rutin wherein $4^G$-alpha-D-glucopyranosyl rutin is crystallized in a supersaturated solution in an organic solvent, and the resultant crystal is recovered.

Such crystallization is feasible with any solution of an organic solvent regardless of the preparation of $4^G$-alpha-D-glucopyranosyl rutin, as long as the solution contains a supersaturated and crystallizable $4^G$-alpha-D-glucopyranosyl rutin.

Usually, the degree of supersaturation is set to about 1.05–1.5. More particularly, a $4^G$-alpha-D-glucopyranosyl rutin specimen, purity of 80% or higher, is dissolved in an organic solvent to give a concentration of about 15–50 w/w %, and the temperature is set to a level which causes a relatively small loss on heat and organic solvent in processing steps, desirably, 0–80° C. Examples of such an organic solvent is methanol, ethanol and aceton, which can be freely added with an appropriate amount of water, if necessary.

Crystallization process is usually carried out by placing a supersaturated solution at a relatively high temperature in a crystallizer, adding thereto a seed, desirably, in an amount of 0.1–5.0 w/w %, and gradually cooling the solution while accelerating its crystallization by gentle stirring.

To obtain a powdery $4^G$-alpha-D-glucopyranosyl rutin, the resultant massecuite is separated, for example, with a basket-type centrifuge into a mother liquor and crystalline $4^G$-alpha-D-glucopyranosyl rutin which is, if necessary, washed by spraying thereto a small amount of a cold organic solvent to further augment the purity, and dried by heating to completely remove the organic solvent. Although the properties of the obtained $4^G$-alpha-D-glucopyranosyl rutin slightly vary dependently on the its purity, it is substantially non-hygroscopic, free-flowing, and free from adhesion and consolidation. Some features of $4^G$-alpha-D-glucopyranosyl rutin are listed in the below:

(1) Its water-solubility at ambient temperature is about thirty thousand-fold or much higher than rutin About 4.3 g $4^G$-alpha-D-glucopyranosyl rutin dissolves in 1 ml water, while only 1 g rutin dissolves in 8 liters of water.

(2) Its molecular absorption coefficient or degree of yellowness is substantially the same as that of rutin.

(3) It has a strong antioxidant activity. Because of this, it is favorably usable as an anti-oxidant in fatty foodstuffs, and pharmaceuticals for susceptive diseases and cosmetics containing oils and fats to prevent their oxidation. Particularly when used in such a pharmaceutical, $4^G$-alpha-D-glucopyranosyl rutin acts as an antioxidant to exhibit activities of removing activated oxygen and suppressing the formation of lipoperoxides, and this is convenient in the prevention and treatment of susceptive diseases and the maintenance and promotion of health. Unlike conventional antioxidants such as vitamin E and vitamin C, $4^G$-alpha-D-glucopyranosyl rutin is substantially odorless and tasteless, and usable without fear of causing undesired coloration, browning and unpleasant odor.

(4) It is hydrolyzable into rutin and glucose by the in vivo enzyme system to exhibit the physiological activity inherent to rutin, in particular, vitamin P activity. Combination with vitamin C augments the physiological activities of both vitamins.

(5) When a $4^G$-alpha-D-glucopyranosyl rutin product additionally contains glucose, the $4^G$-alpha-D-glucopyranosyl rutin component exhibits its inherent activities, while the glucose exhibits shape-imparting, filling and sweetening activities. A product free from glucose is substantially tasteless and odorless, and exhibits the activity of $4^G$-alpha-D-glucopyranosyl rutin without causing substantial shape-imparting and increase in quantity. Thus, the product is freely usable in seasoning and flavoring.

Because of these, $4^G$-alpha-D-glucopyranosyl rutin can be favorably incorporated as a yellow coloring agent, anti-oxidant, stabilizer, quality-improving agent, uv-absorbent, preventive and remedy for susceptive diseases such as viral diseases, bacterial diseases, circulatory diseases and malignant tumors alone or in combination with one or more ingredients, desirably, in an amount of 0.001 w/w % or more in foods, beverages, tobaccos, cigarets, feeds, pet foods, pharmaceuticals for susceptive diseases, cosmetics such as skin-refining agents and skin-whitening agents, and plastics, as well as in agents which are directed to enrich a highly-safe, natural vitamin P. In this case, $4^G$-alpha-D-glucopyranosyl rutin is favorably usable in combination with quercetin, rutin, maltosyl rutin, maltotriosyl rutin, maltotetraosyl rutin and/or malto-pentaosyl rutin.

Since $4^G$-alpha-D-glucopyranosyl rutin is highly resistant to acid and heat, and well harmonizes with various substances which taste sour, salty, bitter, delicious and astringent, it can be favorably incorporated as a vitamin P-enriching agent, yellow coloring agent, anti-oxidant, quality-improving agent and stabilizer in foods and beverages in general, for example, seasonings such as soy sauce, say sauce powder, miso, miso powder, "moromi", "hishio", "furikake", mayonnaise, dressing, vinegar, "sanbai-zu", "funmatsu-sushisu", "chuka-no-moto", "tentsuyu (soup for tenpura)", "mentsuyu (soup for Japanese-style noodles)", Worcester sauce, ketchup, "yakiniku-no-tare (soup for grilled meat)", curry roux, stew premix, soup premix, "dashi-no-moto", mixed seasoning, "mirin (heavily sweetened sake)", "shin-mirin (synthetic mirin)", table sugar and coffee sugar; Japanese-style confectioneries such as "senbei (rice crackers)", "arare (pellet-shaped senbei)", "okoshi (millet-and rice cracker)", "karinto (fried dough cookie)", "gyuhi (starch paste)", rice paste, "manju (bun with a bean-jam filling)", "uiro (sweet rice jelly)", "an (bean jam)", "yokan (sweet jelly of beans)", "mizu-yokan (soft adzuki-bean jelly)", "kingyoku", jelly, castella and "amedama (Japanese-style toffee)"; Western-style confectioneries such as bun, biscuit, cracker, cookie, pie, pudding, cream puff, waffle, sponge cake, doughnut, chocolate, chewing gum, caramel and candy; ice cream and sherbet; syrups such as those for fruit preserve and "kaki-gori (shaved ice)"; spreads and pastes such as butter cream, custard cream, flour paste and fruit paste; processed fruits such as jam, marmalade, fruit syrup and preserved fruit; processed foods such as those of fruits and vegetables; cereals such as bakery product, noodle, vermicelli, boiled rice and synthetic meat; fatty food substances such as salad oil and margarine; pickled products such as "fukujin-zuke (sliced vegetables picked in soy sauce)", "bettara-zuke (fresh radish pickles)", "senmai-zuke" and "rakkyo-zuke (pickled shallots)"; premixes for pickled products such as "takuan-zuke-no-moto" and "hakusai-zuke-no-moto"; meat products such as ham and sausage; fish meat products such as fish meat ham, fish meant sausage, "kamaboko (boiled fish paste)", "chikuwa (literally bamboo wheels)" and "hanpen"; relishes such as "uni-no-shiokara (salted guts of sea urchin)", "ika-no-shiokara (salted guts of squid)", "su-konbu", "saki-surume" and "fugu-no-mirin-boshi"; "tsukudani (food boiled down in soy sauce)" such as those of "nori (dried seaweed)", "sansai (mountain vegetables)", "surume (dried squid)", small fish and shellfish; daily dishes such as "nimame (cooked beans)", potato salad, "konbu-maki (tangle roll)" and "tenpura (deep-fried foods)"; egg and milk products such as "kinshi-tamago", milk beverage, butter and cheese; bottled and canned products such as those of meat, fish meat, fruit and vegetable; alcoholic drinks such as synthetic sake, "zojo-shu", liqueur, wine and whisky; beverages such as coffee, cocoa, juice, carbonated beverage, lactic acid beverage and lactobacillus beverage; premixes and instant foodstuffs such as pudding premix, hot cake premix, instant juice, instant coffee and "sokuseki-shiruko (premix of adzukibean soup with rice cake)". Furthermore, $4^G$-alpha-D-glucopyranosyl rutin can be favorably incorporated as a vitamin P-enriching agent, antioxidant and taste-improving agent in feeds and pet foods for domestic animals and poultries including pet animals such as honey bee, silkworm and pet fish.

In addition to the use as a uv-absorbent and deterioration-preventing agent for plastics, $4^G$-alpha-D-glucopyranosyl rutin can be favorably incorporated in tobaccos, cigarets, pharmaceuticals including preventive and remedy for susceptive diseases, and cosmetics including skin-refining agent and skin-whitening agent in solid, paste or liquid; for example, tobacco, cigaret, troche, cod-liver oil drop, vitamin composition, oral refreshing agent, cachou, gargle, intubation nutrient, internal medicine, injection, dentifrice, lipstick, eye shadow, milky lotion, astringent, cosmetic cream, foundation, sun-screening, cream shampoo and rinse.

The wording "susceptive diseases" as referred to in the invention means those which are prevented and/or treated with $4^G$-alpha-D-glucopyranosyl rutin; for example, viral diseases, bacterial diseases, traumatic diseases, immunopathies, rheumatism, diabetes, circulatory diseases and malignant tumors. The shape and form of pharmaceuticals for susceptive diseases can be freely chosen to meet to their final use; for example, liquid pharmaceuticals such as nebula, collyrium, collunarium, collutory and injection, paste pharmaceuticals such as ointment, cataplasm and cream, and solid pharmaceuticals such as powder, granule, capsule and tablet.

In the preparation of such a pharmaceutical, one or more ingredients, for example, remedy, biologically-active substance, antibiotic, adjuvant, filler, stabilizer, coloring agent and flavoring agent, can be suitably used in combination, if necessary.

The dose is adequately changed dependent on the $4^G$-alpha-D-glucopyranosyl rutin content, administration route and administration frequency; usually, about 0.001–50.0 g/day/adult as $4^G$-alpha-D-glucopyranosyl rutin.

Cosmetics can be prepared similarly as in pharmaceuticals.

In use, $4^G$-alpha-D-glucopyranosyl rutin is incorporated in products by conventional methods, for example, mixing, kneading, dissolving, soaking, permeating, spreading, applying, spraying and injecting, before completion of their processing.

The following experiments will explain in detail the $4^G$-alpha-D-glucopyranosyl rutin of the invention.

EXPERIMENT 1

Preparation of $4^G$-alpha-D-glucopyranosyl rutin

One part by weight of rutin and 10 parts by weight dextrin (DE 12) were mixed in 100 parts by weight of, 80° C. water to obtain a high-rutin content liquid in suspension to which was then added 20 units/g dextrin of cyclomaltodextrin glucanotransferase derived from *Bacillus stearothermophilus*, commercialized by Hayashibara Biochemical Laboratories, Inc., Okayama, Japan, and allowed to react for 64 hours while keeping the liquid at pH 6.0 and 75° C. Paper-chromatographic analysis of the reaction mixture revealed that a major part of the rutin was converted into alpha-glycosyl rutin which bound equimolar or more glucose residues. Thereafter, the reaction mixture was heated to inactivate the remaining enzyme and filtered, after which the filtrate was concentrated to about 30 w/w %, adjusted to pH 5.0, added with 100 units/g solid of glucoamylase (EC 3.2.1.3) commercialized by Seikagaku-Kogyo Co., Ltd., Tokyo, Japan, and allowed to react at 50° C. for 5 hours. Paper-chromatographic analysis of the reaction mixture revealed that it contained a large amount of $4^G$-alpha-D-glucopyranosyl rutin and a small amount of rutin.

Thereafter, the reaction mixture was heated to inactivate the remaining enzyme and filtered, after which the filtrate was applied to a column of "HP-10", a synthetic macroreticular resin commercialized by Mitsubishi Chemical Industries Ltd., Tokyo, Japan, at a flow rate of SV 1.5. The column was then washed with water to remove concomitants including glucose, and applied with an aqueous ethanol to elute $4^G$-alpha-D-glucopyranosyl rutin and intact which were then recovered, concentrated in vacuo and pulverized. The powder was dissolved in a hot water to about 40 w/w % by heating, added with a small amount of a crystalline rutin seed, gradually cooled over a period of 2 days while stirring, and fed to a centrifuge to remove the resultant crystalline rutin. The supernatant was concentrated and pulverized to obtain a powder with a high $4^G$-alpha-D-glucopyranosyl rutin content in the yield of about 70% against the weight of the starting rutin, on the dry solid basis (d.s.b.).

The product contained about 94% $4^G$-alpha-D-glucopyranosyl rutin, d.s.b.

EXPERIMENT 2

Preparation of a high-purity $4^G$-alpha-D-glucopyranosyl rutin

A small portion of a $4^G$-alpha-D-glucopyranosyl rutin powder obtained by the method in Experiment 1 was placed in a glass vessel, and dissolved in an aqueous ethanol (ethanol: water=4:1) to give a concentration of about 35 w/w %. A 5-day standing at ambient temperature resulted in the crystallization on the inside wall of vessel.

The crystal was added to a 40 w/w % $4^G$-alpha-D-glucopyranosyl rutin solution similarly prepared with an aqueous ethanol, and crystallized over a period of 2 days under gentle stirring conditions. Thereafter, the resultant massecuite was separated to obtain crystals which were then washed by spraying thereto a small amount of an aqueous ethanol. Thus, a crystalline $4^G$-alpha-D-glucopyranosyl rutin was obtained. The product was then dissolved in an aqueous ethanol and recrystallized similarly as above, and a crystalline $4^G$-alpha-D-glucopyranosyl rutin was recovered by the separation from the newly formed massecuite, and dried in vacuo at 80° C. overnight. Thus, a $4^G$-alpha-D-glucopyranosyl rutin powder, purity of about 99.8%, was obtained.

Characterization of the powder confirmed that it was a hitherto unknwon $4^G$-alpha-D-glucopyranosyl rutin.

The physicochemical properties will be described hereinafter:

(1) Elemental analysis
  Observed: C=51.2%, H=5.3%
  Calculated: C=51.30%, H=5.22%
    (Chemical formula: $C_{33}H_{40}O_{21}$)

(2) Molecular weight
  772.7

(3) Melting point
  232-235° C. Decomposition)

(4) Specific rotation
  $[\alpha]_D^{20} = 65.3°$ (c=3.67, $H_2O$)

(5) uv-Absorption spectrum
  The present substance was dissolved in an acetic acid-acidified ethanol (acetic acid:ethanol=1: 1,000) to give a concentration of 0.04mM, and the solution was fed to a uv-spectrometer. The result was as shown in FIG. 1.

Figure 2:
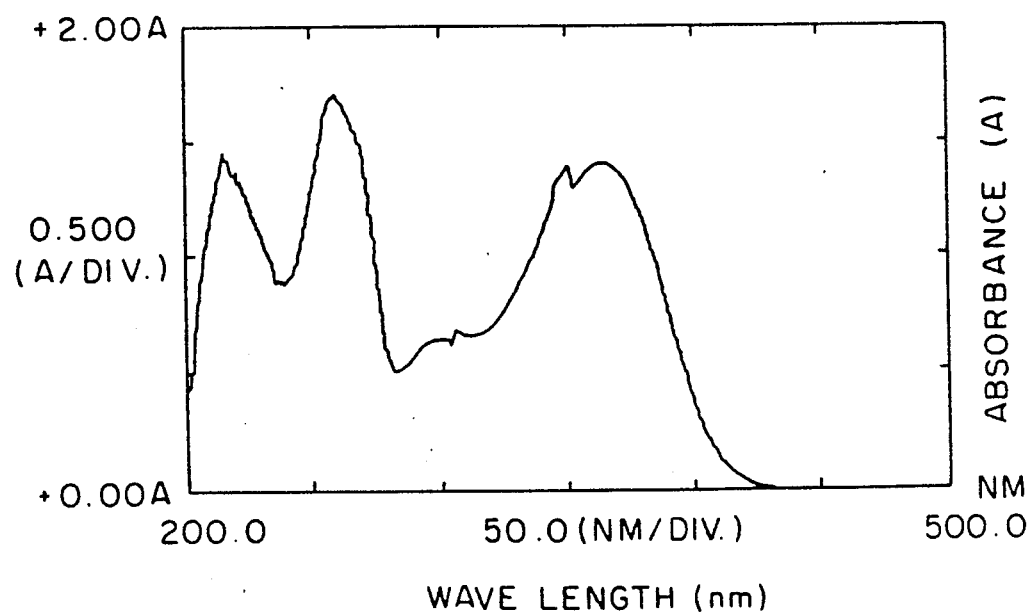
FIG. 2 shows a uv-absorption spectrum of intact rutin (control).

As the control, rutin was dissolved to the same concentration, and fed to the uv-spectrometer. The result was as shown in FIG. 1. The result was as shown in FIG. 2. The results in FIGS. 1 and 2 confirm that the molecular absorption coefficient ($\epsilon$) of the present substance at its absorption peak (362. 5 nm) is $3.50 \times 10^4$ which is substantially the same as that of the control.

Figure 3:
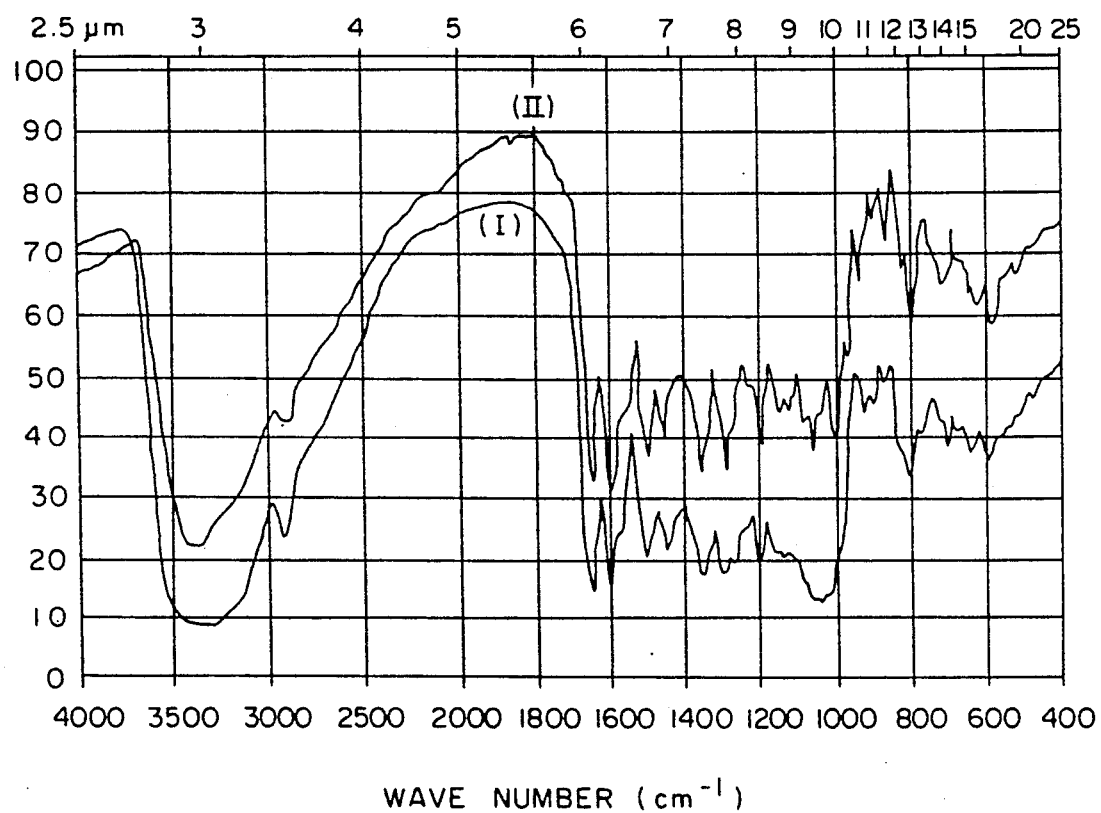
FIG. 3 shows infrared absorption spectra, wherein the spectrum (I) is for $4^G$-alpha-D-glucopyranosyl rutin of the invention, while the other spectrum with the reference numeral (II) is for intact rutin (control).

(6) Infrared absorption spectrum
  The KBr method was employed. The result was as shown in FIG. 3. The infrared absorption spectra of the present substance and rutin (control) are shown with the reference numerals (I) and (II) respectively.

(7) Solubility in solvent
  Readily soluble in water, acetic acid, 0.1 N sodium hydroxide, and 0.1 N hydrochloric acid. Soluble in methanol and ethanol. Hardly soluble in chloroform and ethyl acetate.

(8) Solubility
  One ml water dissolves about 4.3 g of the present substance at 25° C. Only 1 g rutin (control) dissolves in 8 liters of water. These confirm that the solubility of the present substance is improved by about thirty thousand-folds as compared to that of rutin.

(9) Physical properties and color
  Substantially tasteless, odorless yellow powder. Non-hygroscopic and non-deliquescent. Neutral or slightly acidic in aqueous solution.

(10) Stability
  Superiorily stable at pH 3-7 in aqueous solution.

(11) Coloring reaction
  Turning green on the anthrone-sulfuric acid reaction.
  Negative to the Fehling's reaction.

(12) Chemical structure
  (a) Hydrolysis
    i) Hydrolysis with 1N hydrochloric acid yields 1 mole of L-rhamnose and 2 moles of D-glucose per mole of quercetin.
    ii) Hydrolysis using an alpha-glucosidase derived from pig liver yields 1 mole of glucose per mole of rutin.
  (b) NMR spectrum The present substance and rutin were determined in dimethyl silfoxide (DMSO) for their nmr spectra with "VXR-500", an nmr spectrometry commercialized by Varian Associates, Palo Alto, California, USA. The results were as shown in Table I.

TABLE I

| Carbon number | Rutin Authentic | Rutin Observed | Present substance Observed | Difference |
|---|---|---|---|---|
| *Quercetin structure* | | | | |
| 2 | 156.4 | 156.2 | 156.1 | 0.1 |
| 3 | 133.6 | 133.0 | 132.9 | 0.1 |
| 4 | 177.4 | 177.1 | 176.7 | 0.4 |
| 5 | 156.6 | 156.4 | 156.4 | 0.0 |
| 6 | 98.8 | 98.5 | 99.2 | −0.7 |
| 7 | 164.0 | 163.9 | 166.6 | −2.7 |
| 8 | 93.6 | 93.4 | 93.8 | −0.4 |
| 9 | 161.2 | 161.0 | 160.9 | 0.1 |
| 10 | 105.2 | 103.7 | 102.8 | 0.9 |
| 1' | 121.6 | 120.9 | 120.7 | 0.2 |
| 2' | 115.3 | 115.0 | 115.1 | −0.1 |
| 3' | 144.6 | 144.5 | 144.6 | −0.1 |
| 4' | 148.3 | 148.2 | 148.6 | −0.4 |
| 5' | 116.5 | 116.0 | 115.8 | 0.2 |
| 6' | 121.6 | 121.3 | 121.3 | 0.0 |
| *Glucose residue in rutinose moiety* | | | | |
| 1 | 100.7 | 100.5 | 100.6 | −0.1 |
| 2 | 74.2 | 73.8 | 73.4 | 0.4 |
| 3 | 76.8 | 76.2 | 75.9 | 0.3 |
| 4 | 70.4 | 70.1 | 79.8 | −9.7 |
| 5 | 76.1 | 75.7 | 73.7 | 2.0 |
| 6 | 67.1 | 66.8 | 66.5 | 0.3 |
| *Rhamnose residue in rutinose moiety* | | | | |
| 1 | 101.5 | 100.9 | 101.1 | −0.2 |
| 2 | 70.4 | 70.3 | 70.3 | 0.0 |
| 3 | 70.8 | 69.8 | 69.3 | 0.5 |
| 4 | 72.2 | 71.6 | 71.6 | 0.0 |
| 5 | 68.2 | 68.2 | 68.1 | 0.1 |
| 6 | 17.5 | 17.5 | 17.5 | 0.0 |
| *New glucose residue* | | | | |
| 1 | | | 101.2 | |
| 2 | | | 73.0 | |
| 3 | | | 73.3 | |
| 4 | | | 69.8 | |
| 5 | | | 72.2 | |
| 6 | | | 60.3 | |

Note:
The authentic data are cited from K. R. Markham, Tetrahedron, Vol. 32, pp. 2,607–2,612 (1976). The difference in chemical shift is calculated with the observed data for the present substance and rutin.

As shown in Table I, the face that a large chemical shift was found only at the 4-position of the glucose residue in rutin suggests that the transferred glucose residue is bound at the 4-position of the glucose residue in the rutinose residue via ether binding.

The above physicochemical properties confirm that the present substance is $4^G$-alpha-D-glucopyranosyl rutin, a novel substance shown by the formula [I]:

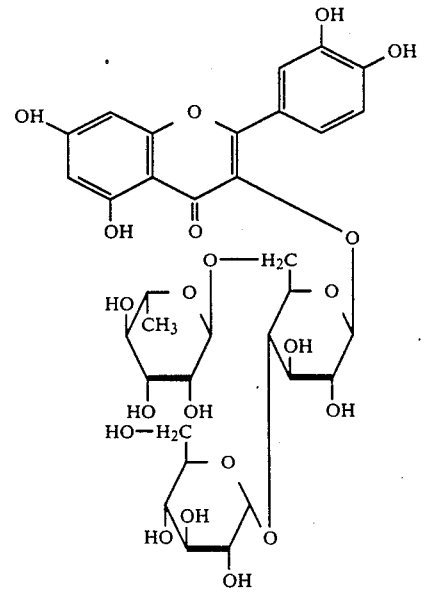

The above results confirm that the alpha-glycosyl rutin binding equimolar or more glucose residues, which is formed by allowing cyclomaltodextrin glucanotransferase to act on a solution containing rutin together with an amylaceous substance has a structure shown by the formula [III]:

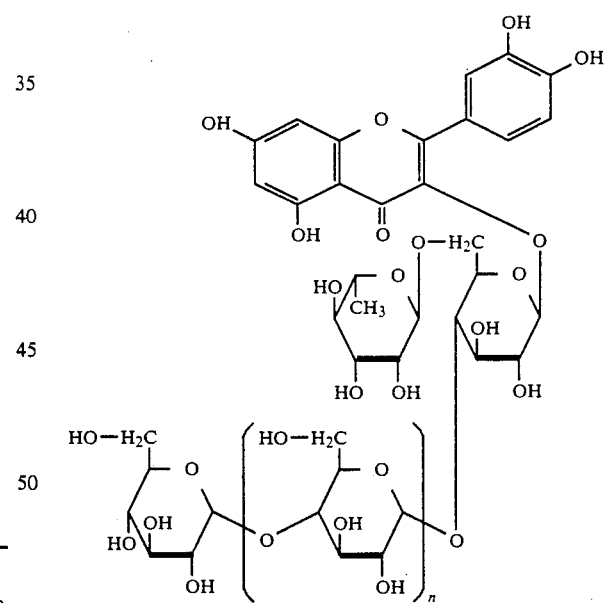

wherein n is an integer from 0 to 15.

EXPERIMENT 3

Antioxidant activity of $4^G$-alpha-D-glucopyranosyl rutin $4^G$-Alpha-D-glucopyranosyl rutin was tested for antioxidant activity on powdered peanut butter which is used an example of fatty food substances highly susceptive to oxidation.

One hundred parts by weight of a peanut butter was added with 83 parts by weight of "FINETOSE®", a crystalline alpha-maltose commercialized by Hayashibara Co., Ltd., Okayama, Japan, 9.6 parts by weight of water, and, as an antioxidant, either 0.5 parts by weight of a high-purity $4^G$-alpha-D-glucopyranosyl rutin powder obtained by the method in Example A-4, or a mixture of 0.5 parts by weight of the high-purity $4^G$-alpha-D-glucopyranosyl rutin and 0.2 parts by weight of citric acid. The mixture was placed in a tray, sealed, solidified by allowing it to stand at 35° C. for 1 day, and prepared into a powder which was then placed in aluminum cups and allowed to stand in a 35° C. incubator without sealing. During the standing, the contents in the aluminum cups were periodically checked for their peroxide value. Peroxide value (meg/kg) was determined in accordance with the method in D.H.Wheeler, *Oil and Soap*, Vol.9, pp.89–97 (1932) with a slight modification.

As the control, a group with no antioxidant was tested similarly as above.

The results were as shown in Table II.

TABLE II

| Antioxidant | Time period (days) | | | | |
|---|---|---|---|---|---|
| | 0 | 8 | 27 | 42 | 55 |
| No addition | 3.89 | 11.1 | 71.8 | 98.6 | 130.0 |
| $4^G$-Alpha-D-glucopyranosyl rutin | 1.78 | 5.53 | 14.6 | 23.4 | 32.5 |
| $4^G$-Alpha-D-glucopyranosyl rutin + citric acid | 1.32 | 3.26 | 6.05 | 11.6 | 17.2 |

The results in Table II confirm that in comparison to the control, $4^G$-alpha-D-glucopyranosyl rutin has a stronger antioxidant activity, which is further augmented by combination with citric acid.

EXPERIMENT 4

Acute toxicity

A $4^G$-alpha-D-glucopyranosyl rutin powder, obtained by the method in Example A-3, was orally administered to 7-week old dd mice for acute toxicity test. As the result, no mouse died when administered with up to 5 g $4^G$-alpha-D-glucopyranosyl rutin, and higher dose was difficult.

These confirmed that the powdery substance was extremely low in toxicity.

A high-purity $4^G$-alpha-D-glucopyranosyl rutin powder, obtained by the method in Example A-4, was tested similarly as above to obtain the same result, confirming that the toxicity of this powdery substance was extremely low.

The following Examples A and Examples B will illustrate the preparation and uses of $4^G$-alpha-D-glucopyranosyl rutin respectively.

EXAMPLE A-1

$4^G$-Alpha-glucopyranosyl rutin

One part by weight of rutin was dissolved in 5 parts by weight of 50 v/v % aqueous ethanol by heating solution was mixed with another solution which had been separately prepared by dissolving 8 parts by weight of dextrin (DE 8) in 45 parts by weight of water by heating. The mixture was added with 10 units/g dextrin of cyclomaltodextrin glucano-transferase derived from *Bacillus stearothermoph* commercialized by Hayashibara Biochemical Laboratories, Inc., Okayama, Japan, adjusted to pH 6.0 and allowed to react at 50° C. for 48 hours. Paper-chromatographic analysis of the reaction mixture revealed that a major part of the rutin was converted into $4^G$-alpha-D-glucopyranosyl rutin binding equimolar or more glucose residues.

Thereafter, the reaction mixture was concentrated in vacuo to distill out the ethanol, heated to inactivate the remaining enxyme, adjusted to pH 5.0, added with 100 units/g solid of glucoamylase (EC 3.2.1.3) commercialized by SeikagakuKogyo Co., Ltd., Tokyo, Japan, and allowed to react at 50° C. for 5 hours. The newly formed reaction mixture was then heated to inactivate the remaining enzyme and filtered, after which the filtrate was deionized and purified with ion exchanges (H- and OH-forms), and concentrated to obtain a syrupy product containing about 10 w/w % $4^G$-alpha-D-glucopyranosyl rutin together with a small amount of rutin and a large amount of glucose in the yield of about 95% against the weight of the starting material, d.s.b.

The product is favorably usable as a highly-safe, natural yellow coloring agent, antioxidant, stabilizer, quality-improving agent, preventive, remedy and uv-absorbent in foods, beverages, tobaccos, cigarets, feeds, pet foods, pharmaceuticals for susceptive diseases, cosmetics and plastics, in addition to the use in an agent directed to enrich a readily water-soluble vitamin P.

EXAMPLE 2

EXAMPLE A-2(1)

Preparation of alpha-glucosidase

*Mucor javanicus* IFO 4570 was inoculated and cultivated at 30° C. for 44 hours under aeration-agitation conditions in 500 parts by weight of a liquid culture medium which contained water together with 4.0 w/v % maltose, 0.1 w/v % potassium phosphate monobasic, 0.1 w/v % ammonium nitrate, 0.05 w/v % magnesium sulfate, 0.05 w/v % potassium chloride, 0.2 w/v % polypeptone and 1 w/v % calcium carbonate which had been sterilized by heating and sterilely added to the water immediately before the innoculation.

After completion of the cultivation, the mycelia was collected from the culture, added with 500 parts by weight of 4M urea in 0.5M acetate buffer (pH 5.3) per 48 parts by weight of the wet mycelia, allowed to stand at 30° C. for 40 hours and centrifuged. The supernatant was dialyzed against flowing water overnight, added with ammonium sulfate to 0.9 saturation, and allowed to stand at 4° C. overnight, after which the resultant sediment was collected, suspended in 50 parts by weight of 0.01M acetate buffer (pH 5.3) and centrifuged. The supernatant was used as an alpha-glucosidase specimen.

EXAMPLE A-2(2)

Preparation of $4^G$-alpha-D-glucopyranosyl rutin

Four parts by weight of rutin was dissolved in 40 parts by weight of 0.5N sodium hydroxide solution by heating adjusted to pH 6.5 with 5N hydrochloric acid, and mixed with another solution which had been separately prepared by dissolving 20 parts by weight of dextrin (DE 30) in 10 parts by weight of water by heating. The obtained high-rutin content liquid in suspension was added with 10 parts by weight of an alpha-glucosidase specimen obtained by the method in Example A-2(1), and allowed to react for 40 hours under stirring condition while keeping the liquid at pH 6.5 and 55° C.

Thereafter, the reaction mixture was heated to inactivate the remaining enzyme, adjusted to pH 5.0, and subjected to glucoamylase similarly as in Example A-1.

The newly formed reaction mixture was heated to inactivate the remaining enzyme and filtered, after which the filtrate was applied to a column of "HP-10", a synthetic macroreticular resin commercialized by Mitsubishi Chemical Industries Ltd., Tokyo, Japan, at a flow rate of SV 2. As the result, the column adsorbed a large amount of $4^G$-alpha-D-glucopyranosyl rutin and a small amount of the remaining rutin both present in the reaction mixture, while glucose and salts flew out through the column without causing adsorption. The column was then washed with water and applied with an aqueous ethanol to elute the $4^G$-alpha-D-glucopyranosyl rutin which was then collected, concentrated in vacuo and pulverized to obtain a powdery product containing about 75 w/w % $4^G$-alpha-D-glucopyranosyl rutin together with rutin in the yield of about 90% against the weight of the starting rutin, d.s.b.

The product is favorably usable as a highly-safe, natural yellow coloring agent, antioxidant, stabilizer, quality-improving agent, preventive, remedy, uv-absorbent and deterioration-preventing agent in foods, beverages, tobaccos, cigarets, feeds, pet foods, pharmaceuticals for susceptive diseases, cosmetics and plastics, in addition to the use in an agent directed to enrich a highly water-soluble vitamin P.

EXAMPLE A-3

$4^G$-Alpha-D-glucopyranosyl rutin

One part by weight of rutin and 10 parts by weight of dextrin (DE 12) were mixed in 98 parts by weight of hot water to obtain a high-rutin content liquid in suspension which was then added with 20 units/g dextrin of cyclomaltodextrin glucanotransferase, and allowed to react for 64 hours under stirring conditions while keeping the liquid at pH 6.0 and 75° C. Paper-chromatographic analysis of the reaction mixture revealed that a major part of the rutin was converted into an alpha-glycosyl rutin which bound equimolar or more glucose residues. Thereafter, the reaction mixture was heated to inactivate the remaining enzyme, adjusted to pH 5.0, and subjected to glucoamylase similarly as in Example A-1.

The newly formed reaction mixture was heated to inactivate the remaining enzyme and filtered, after which the filtrate was applied to a column of "HP-20", a synthetic macroreticular resin commercialized by Mitsubishi Chemical Industries Ltd., Tokyo, Japan, at a flow rate of SV 1.5. As the result, the column adsorbed the $4^G$-alpha-D-glucopyranosyl rutin and remaining rutin in the reaction mixture, while glucose and salts flew out through the column without causing adsorption. The column was then washed with water and applied with an aqueous ethanol to elute the $4^G$-alpha-D-glucopyranosyl rutin which was then collected, concentrated in vacuo and pulverized. The resultant powder was dissolved in a hot water to about 50 w/w % by heating, added with a small amount of a crystalline rutin seed, crystallized by stirring, and fed to a centrifuge to remove the resultant crystalline rutin. The supernatant was concentrated and pulverized to obtain a powdery $4^G$-alpha-D-glucopyranosyl rutin product, purity of about 95%, in the yield of about 90% against the weight of the starting rutin, d.s.b.

Similarly as the product in Example A-2, the product is favorably usable as a highly-safe, natural yellow coloring agent, antioxidant, stabilizer, quality-improving agent, preventive, remedy, uv-absorbent and deterioration-preventing agent in foods, beverages, tobaccos, cigarets, feeds, pet foods, pharmaceuticals for susceptive diseases, cosmetics and plastics, in addition to the use in an agent directed to enrich a readily water-soluble vitamin P.

EXAMPLE A-4

High-purity $4^G$-alpha-D-glucopyranosyl rutin

A $4^G$-alpha-D-glucopyranosyl rutin product obtained by the method in Example A-3 was placed in a glass vessel, dissolved in methanol to give a concentration of 25 w/w % by heating, and allowed to stand at ambient temperature for 3 days. Thus, crystallization occurred on the inside wall of the vessel. An about 30 w/w % solution of a fresh preparation of the same $4^G$-alpha-D-glucopyranosyl rutin product in methanol was added with the obtained crystal as the seed, and crystallized over a period of 2 days by gentle stirring, followed by the separation of the resultant massecuite. The obtained crystal was washed by spraying thereto a small amount of methanol, and dried in vacuo at 70° C. overnight to obtain a $4^G$-alpha-D-glucopyranosyl rutin powder with a purity of about 99%.

The product, a high-purity 4-alpha-D-glucopyranosyl rutin, is favorably usable as a highly-safe, natural yellow coloring agent, antioxidant, stabilizer, quality-improving agent, preventive, remedy, uv-absorbent and deterioration preventing agent in foods, beverages, tobaccos, cigarets, feeds, pet foods, pharmaceuticals for susceptive diseases, cosmetics and plastics, in addition to the use in an agent directed to enrich a readily water-soluble vitamin P.

Figure 4:
FIG. 4 is a microscopic view illustrating the crystallization of $4^G$-alpha-D-glucopyranosyl rutin in a solution containing methanol ($\times 40$).

FIG. 4 is a microscopic view illustrating the crystallization in a solution containing methanol.

Analysis of the crystal using "GEIGERFLEX RAD-II B (CuKα)", a powder x-ray diffractometer commercialized by Rigaku Corp., Tokyo, Japan, revealed predominant diffraction angles ($2\theta$) of 4.4°, 8.4°, 11.5° and 18.2°. The fact that heat-drying readily converted the crystal into an amorphous powder having no such a diffraction angle suggests that the crystal would be a complex crystal between $4^G$-alpha-D-glucopyranosyl rutin and methanol.

EXAMPLE A-5

$4^G$-Alpha-D-glucopyranosyl rutin

A high-rutin content liquid, obtained by mixing 1 part by weight of rutin, 5 parts by weight of dextrin (DE 8) and 50 parts by weight of water, and dissolving them as much as dextrin of cyclomaltodextrin glucanotransferase, and allowed to reacted for 40 hours under stirring while keeping the liquid at pH 6.5 and 70° C.

The reaction mixture was treated to inactivate the remaining enzyme, adjusted to pH 5.0, and subjected to glucoamylase similarly as in Example A-1. The newly formed reaction mixture was heated to inactivate the remaining enzyme and filtered, after which the filtrate was applied to a column of "XAD-7", a synthetic macroreticular resin, commercialized by Rohm & Haas Company, Philadelphia, USA, at a flow rate of SV 1.5.

As the result, the column adsorbed the $4^G$-alpha-D-glucopyranosyl rutin and remaining rutin both present in the reaction mixture, while glucose and salts flew out through the column without causing adsorption.

The column was then washed with water and applied with an aqueous ethanol having a stepwisely increasing concencentration to obtain fractions rich in $4^G$-alpha-D- glucopyranosyl rutin which were then concentrated and pulverized to obtain a powdery $4^G$-alpha-D-glucopyranosyl rutin product with a purity of about 93% in the yield of about 85% against the weight of the starting rutin, d.s.b.

Similarly as the product in Example A-2, the product is favorably usable as a highly-safe, natural yellow coloring agent, antioxidant, stabilizer, quality-improving agent, preventive, remedy, uv-absorbent and deterioration-preventing agent in foods, beverages, tobaccos, cigarets, feeds, pet foods, pharmaceuticals for susceptive diseases, cosmetics and plastics, in addition to the use in an agent directed to enrich a readily water-soluble vitamin P.

EXAMPLE A-6

High-purity $4^G$-alpha-D-glucopyranosyl rutin

A $4^G$-alpha-glucopyranosyl rutin product obtained by the method in Example A-5 was dissolved in an aqueous ethanol (ethanol:water=4:1) to give a concentration of 43 w/w % by heating, and the solution was added with 0.5 w/w % of a crystal obtained by the method in Experiment 2 as the seed, and crystallized over a period of 2 days by gentle stirring, followed by the separation of the resultant massecuite. The obtained crystal was washed by spraying thereto a small amount of an aqueous ethanol, and dried in vacuo at 80° C. overnight to obtain a $4^G$-alpha-D-glucopyranosyl rutin powder with a purity of about 98%.

The product, a high-purity $4^G$-alpha-D-glucopyranosyl rutin, is favorably usable as a highly-safe, natural yellow coloring agent, antioxidant, stabilizer, quality-improving agent, preventive, remedy, uv-absorbent and deterioration-preventing agent in foods, beverages, feeds, pet foods, pharmaceuticals for susceptive diseases, cosmetics and plastics, in addition to the use in an agent directed to enrich a readily water-soluble vitamin P.

Figure 5:
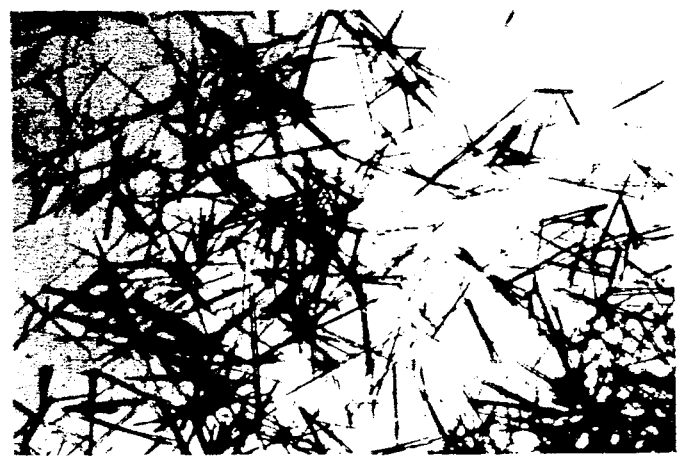
FIG. 5 is a microscopic view illustrating the crystallization of $4^G$-alpha-D-glucopyranosyl rutin in a solution containing ethanol ($\times 40$).

FIG.5 is a microscopic view illustrating the crystallization in an aqueous organic solvent (ethanol:water=4:1).

The crystals were tested with the powder x-ray diffractometer similarly as in Example A-4 to obtain predominant diffraction angles ($2\theta$) of 6.8°, 8.1°, 15.4° and 17.8° which were different from those of the crystal obtained in methanol in Example A-2.

The fact that heat-drying readily converted the crystal into an amorphous powder having no such a diffraction angle suggests that it would be a complex crystal between $4^G$-alpha-D-glucopyranosyl rutin and ethanol.

EXAMPLE B-1

Hard candy

Fifteen hundred parts by weight of "MABIT®", a hydrogenated maltose syrup commercialized by Hayashibara Shoji, Inc., Okayama, Japan, was heated, concentrated to a moisture content below about 2%, and mixed to homogeneity with 15 parts weight of citric acid, 1 part by weight of a $4^G$-alpha-D-glucopyranosyl rutin powder obtained by the method in Example A-3 and a small amount of lemon flavor, after which the mixture was molded and packaged in usual manner to obtain a hard candy.

The product is a yellow colored, vitamin P-enriched, low-cariogenic and low-caloric lemon candy.

EXAMPLE B-2

"Fuki-no-mizuni (Boiled bog rhubarb)"

Fresh bog rhubarbs were pared, cut into short sticks, soaked in a diluted saline, and boiled down in a liquid containing an alpha-glycosyl rutin syrup obtained by the method in Example A-5 and "Aoiro Ichi-go (Blue No. 1)", a green coloring agent, to obtain a freshly green "fuki-no-mizuni".

The product pleases the eyes when arranged in Japanese traditional cuisines, as well as exhibiting physiological activity as a dietary fiber.

EXAMPLE B-3

"Gyuhi (starch paste)"

One part by weight of waxy rice starch was mixed with 1.2 parts by weight of water, and the mixture was mixed to homogeneity with 1.5 parts by weight of sucrose, 0.7 parts by weight of "SUNMALT®", a crystalline beta-maltose commercialized by Hayashibara Co., Ltd., Okayama, Japan, 0.3 parts by weight starch syrup and 0.02 parts by weight of a $4^G$-alpha-D-glucopyranosyl rutin powder obtained by the method in Example A-2 while gelatinizing by heating, molded and packaged in usual manner to obtain "gyuhi".

The product is a Japanese-style confectionery which looks like "kibi-dango (millet dumpling)", and is excellent in flavor and biting properties.

EXAMPLE B-4

Mixed sweetener

A mixed sweetener was obtained by mixing 100 parts by weight of honey, 50 parts by weight of isomerized sugar, 2 parts by weight of "kurozato (unrefined sugar)" and 1 part by 1 weight of a $4^G$-alpha-D-glucopyranosyl rutin syrup obtained by the method in Example A-1.

The product is a vitamin P-enriched sweetener, and suitable for health food.

EXAMPLE B-5

Cream filling

A cream filling was obtained by mixing in usual manner 1,200 parts by weight of "FINETOSE®", a crystalline alpha-maltose commercialized by Hayashibara Co., Ltd., Okayama, Japan, 1,000 parts by weight of shortening, 10 parts by weight of a $4^G$-alpha-D-glucopyranosyl rutin powder obtained by the method in Example A-5, 1 part by weight of lecithin, 1 part by weight of lemon oil and 1 part by weight of vanilla oil to homogeneity.

The product is a yellow colored, vitamin P-enriched cream filling which is excellent in taste, flavor, melting and biting properties, and is prevents oxidation of the fatty ingredients.

EXAMPLE B-6

Orange juice

Fifty parts by weight of a fresh orange juice, 0;1 part of citric acid, 5 parts by weight of sucrose, 0.1 part by weight of a high-purity $4^G$-alpha-D-glucopyranosyl rutin powder obtained by the method in Example A-6, 0.1 part by weight of L-ascorbic acid (vitamin C), flavor and 46 parts by weight of water were mixed, and the mixture was distributed in vessels and pasteurized in the usual manner to obtained the captioned product.

The product is a vitamin P- and vitamin C-enriched orange juice excellent in color, taste and flavor.

EXAMPLE B-7

Tablet

Twenty parts by weight of ascorbic acid was mixed to homogeneity with 13 parts by weight of crystalline beta-maltose, maltose, 4 parts by weight of cornstarch and 3 parts by weight of a $4^G$-alpha-D-glucopyranosyl rutin powder obtained by the method in Example A-2, and the resultant was tabletted with a 20R punch, diameter of 12 mm.

The product is an easily swallowable vitamin composition containing ascorbic acid and alpha-glucosyl rutin, wherein the ascorbic acid is excellently stable.

EXAMPLE B-8

Capsule

Ten parts by weight of calcium acetate monohydrate, 50 parts by weight of magnesium L-lactate trihydrate, 57 parts by weight of maltose, 20 parts by weight of a $4^G$-alpha-D-glucopyranosyl rutin powder obtained by the method in Example A-3, 12 parts by weight of a gamma-cyclodextrin inclusion compound containing 20% eicosapentaenoic acid were mixed to homogeneity, and the mixture was fed to a granulator and encapsulated in gelatine to obtain capsules, 150mg each.

The product is preventive to the oxidation of the eicosapentaenoic acid, and favorably usable as a high-quality blood cholesterol lowering agent, immunopotentiator and skinrefining agent in preventive and remedy for susceptive diseases, as well as in foodstuffs directed to the maintenance and promotion of health.

EXAMPLE B-9

Ointment

One part by weight of sodium acetate trihydrate, 4 parts by weight of DL-calcium lactate and 10 parts by weight of glycerine were mixed to homogeneity, and the mixture was added to another mixture of 50 parts by weight of vaseline, 10 parts by weight of vegetable wax, 10 parts by weight of lanolin, 14.5 parts by weight of sesame oil, part by weight of a high-purity $4^G$-alpha-D-glucopyranosyl rutin powder obtained by the method in Example A-4 and 0.5 parts by weight of peppermint oil, and mixed to homogeneity to obtain an ointment.

The product is antioxidative, highly stable, and favorably usable as a high-quality sun-screening, cream skin-refining agent, skin-whitening agent and promoter for healing injury and burn.

EXAMPLES B-10

Injection

A high-purity $4^G$-alpha-D-glucopyranosyl rutin powder obtained by the method in Example A-4 was dissolved in water, and sterilely filtered in ususal manner to obtain a pyrogen-free solution which was then distributed to 20 ml glass vials to give an alpha-glucosyl rutin content of 200 mg, dried in vacuo and sealed to obtained the captioned product.

The product is intramuscularly and intravenously administrable alone or in combination with vitamins and minerals. The product requires no cold storage, and exhibits an excellently high solubility in saline when in use.

Besides supplementing vitamin P, the product functions as an antioxidant to remove activated oxygen and suppress the formation of lipoperoxides, therefore is favorably usable in preventive and remedy for various diseases including viral diseases, bacterial diseases, circulatory diseases and malignant tumors.

EXAMPLE B-11

Injection

Six parts by weight of sodium chloride, 0.3 parts by weight of potassium chloride, 0.2 parts by weight of calcium chloride, 3.1 parts by weight of sodium lactate, 45 parts by weight of maltose and 2 parts of a high-purity $4^G$-alpha-D-glucopyranosyl rutin powder obtained by the method in Example A-6 were dissolved in 1,000 parts by weight of water, and sterilely filtered in usual manner, after which 250 ml aliquots of the pyrogen-free solution were distributed to sterilized plastic vessels to obtain the captioned product.

The product supplements, in addition to vitamin P, calories and minerals, therefore in suitable for injection directed to remove activated oxygen and to suppress the formation of lipoperoxdes. Thus, the product is favorably usable as a preventative and remedy for various diseases including viral diseases, bacterial diseases, circulatory diseases and malignant tumors, as well as in the restoration of health during and before suffering from diseases.

EXAMPLE B-12

Intubation nutrient

Twenty four gram aliquots of a composition consisting of 20 parts by weight of crystalline alpha-maltose, 1.1 parts by weight of glycine, 0.18 parts by weight of sodium glutamate, 1.2 part by weight of sodium chloride, 1 part by weight of citric acid, 0.4 parts by weight of calcium lactate, 0.1 part by weight of magnesium carbonate, 0.1 part by weight of a $4^G$-alpha-D-glucopyranosyl rutin powder obtained by the method in Example A-5, 0.01 part by weight of thiamine and 0.01 part by weight of riboflavin were packed in laminated aluminum bags, and heat-sealed to obtain the captioned product.

In use, one bag of the product is dissolved in about 300–500 ml of water, and the solution is favorably usable as an intubation nutrient directed to oral and parenteral administration to the nasal cavity, stomach and intestine.

EXAMPLE B-13

Bath liquid

A bath liquid was obtained by mixing 21 parts of Dl-sodium lactate, 8 parts by weight of sodium pyruvate, 5 parts by weight of a $4^G$-alpha-D-glucopyranosyl rutin powder obtained by the method in Example A-3 and 40 parts by weight of ethanol with 26 parts by eight of refined water and appropriate amounts of coloring agent and flavoring agent.

The product is suitable for skin-refining agent and skin-whitening agent, and is diluted by 100–10,000-folds in bath water when in use. The product is favorably usable as cleansing liquid, astringent and moisture liquid.

EXAMPLE B-14

Milky lotion

One half part by weight of polyoxyethylene behenyl ether, 1 part by weight of polyoxyethylene sorbitol tetraoleate, 1 part by weight of oil-soluble glyceryl monostearate, 0.5 parts by weight of pyruvic acid, 0.5 parts by weight of behenyl alcohol, 1 part by weight of avocado oil, 1 part by weight of a high-purity $4^G$-alpha-D-glucopyranosyl rutin powder obtained by the method in Example A-4 and appropriate amounts of vitamin E and antiseptic were dissolved by heating in usual manner, and the solution was added with 1 part by weight of L-sodium lactate, 5 parts by weight of 1,3-butylene glycol, 0.1 part by weight of caoboxyvinyl polymer and 85.3 parts by weight of refined water, emulsified with a homogenizer, added with an appropriate amount of flavoring agent, and mixed by stirring to obtained the captioned product.

The product is antioxidative, highly stable and favorably usable as a high-quality sun-screening, cream skin-refining agent and skin-whitening agent.

EXAMPLE B-15

Cosmetic cream

Two parts by weight of polyoxyethylene glycol monostearate, 5 parts by weight of self-emulsifying glycerine monostearate, 2 parts by weight of a high-purity $4^G$-alpha-D-glucopyranosyl rutin powder obtained by the method in Example A-6, 1 part by weight of liquid paraffin, 10 parts by weight of glyceryl triactanate and a appropriate amount of antiseptic were dissolved by heating in usual manner, and the mixture was added with 2 parts by weight of L-lactic acid, 5 parts by weight of 1,3-butylene glycol and 66 parts by weight of refined water, emulsified with a homogenizer, added with an appropriate amount of flavoring agent, and mixed by stirring to obtained the captioned product.

The product is antioxidative, highly stable and favorably usable as a high-quality sunscreening cream, skin-refining agent and skin-whitening agent.

EXAMPLE B-16

Antioxidant

An antioxidant was prepared by mixing 10 parts by weight of a $4^G$-alpha-D-glucopyranosyl rutin powder obtained by the method in Example A-3, 2 parts by weight of vitamin $E_2$, 0.1 parts by weight of lecithin and 0.5 parts by weight of sodium citrate to homogeneity.

The product is favorably usable as an antioxidant, stabilizer and quality-improving agent in fatty food substances such as margarine and butter cream, pharmaceuticals for susceptive diseases such as unsaturated fatty acids, oil-soluble vitamin and oil-soluble hormones, and cosmetics such as cream lotion and cosmetic cream by incorporating thereto in an amount of about 0.01-5.0 w/w %.

Example B-17

Antioxidant

An antioxidant was prepared by mixing to homogeneity 10 parts by weight of a high-purity $4^G$-alpha-D-glucopyranosyl rutin powder obtained by the method in Example A-6 and 0.2 parts by weight of sodium citrate.

The product is favorably usable as an antioxidant, stabilizer, fading-preventing agent and quality-improving agent in fatty food substances such as margarine and butter cream, pharmaceuticals for alpha-glycosyl rutin-susceptive diseases such as unsaturated fatty facids, oil-soluble vitamin and oil-soluble hormones, and cosmetics such as cream lotion and cosmetic cream by incorporating thereinto in an amount about 0.01-5.0 w/w %. Furthermore, the product is favorably usable as antioxidant, stabilizer, fading-preventing agent and quality-improving agent in foods and beverages containing a readily-fading natural pigment by incorporating thereinto in an amount of about 0.01-2.0 w/w %.

As described above, the novel substance of the invention, $4^G$-alpha-D-glucopyranosyl rutin, is substantially tasteless and odorless, free of toxicity and readily hydrolyzable in vivo into rutin and D-glucose to exhibit the physiological activities inherent to rutin, as well as augmenting the solubility of rutin by thirty thousand-folds or higher while retaining its molecular absorption coefficient or degree of yellowness.

$4^G$-Alpha-D-glucopyranosyl rutin is readily produced with a biochemical process which comprises allowing a saccharide-transferring enzyme and glucoamylase to act on a solution containing rutin together with an amylaceous substance. The process is economically superior, and easily commercializable.

We established both reaction process which provides an increased initial concentration for rutin so as to facilitate the formation of $4^G$-alpha-D-glucopyranosyl rutin at a high concentration, and purification process wherein $4^G$-alpha-D-glucopyranosyl rutin is purified by allowing the reaction mixture to contact with a synthetic macroreticular resin. These facilitate the industrial-scale production of $4^G$-alpha-D-glucopyranosyl rutin.

Furthermore, we established a process to prepare high-purity $4^G$-alpha-D-glucopyranosyl rutin comprising crystalization of $4^G$-alpha-D-glucopyranosyl rutin from a supersaturated solution, and subsequent separation thereof. This process renders the commercialization of high-purity $4^G$-alpha-D-glucopyranosyl rutin very easy.

The $4^G$-alpha-D-glucopyranosyl rutin thus obtained is favorably usable as a yellow coloring agent, antioxidant, stabilizer, quality-improving agent, preventive, remedy, uv-absorbent and deterioration-preventing agent in foods, beverages, tobaccos, cigarets, feeds, pet foods, pharmaceuticals for susceptive diseases, cosmetics including skin-refining agent, melanin formation-suppressing agent and skin-whitening agent, and plastics, in addition to the use in agent directed to enrich a high-safe, natural vitamin P.

Accordingly, the present invention is extremely significant in food, beverage, cosmetic, pharmaceutical and plastic industries in view of the establishment of industrial-scale production and practical uses for $4^G$-alpha-D-glucopyranosyl rutin.

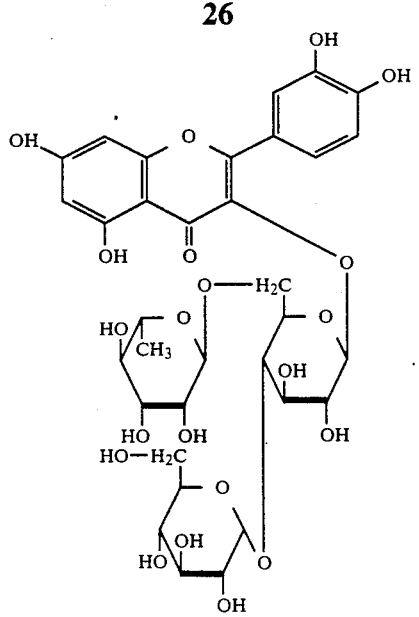

We claim:

1. A substantially pure $4^G$-Alpha-glucopyranosyl rutin shown by the formula [I]: